United States Patent [19]

Takada et al.

[11] Patent Number: 6,024,950

[45] Date of Patent: Feb. 15, 2000

[54] EYELASH COSMETIC COMPOSITION

[75] Inventors: Hirotaka Takada; Yoko Takashima; Akihito Yokotsuka; Yoshikazu Soyama, all of Yokohama, Japan

[73] Assignee: Shiseido Company, Ltd., Tokyo, Japan

[21] Appl. No.: 09/143,380

[22] Filed: Aug. 28, 1998

[30] Foreign Application Priority Data

Aug. 29, 1997 [JP] Japan .................................. 9-249709
Aug. 10, 1998 [JP] Japan ................................ 10-225541
Aug. 20, 1998 [JP] Japan ................................ 10-233747

[51] Int. Cl.[7] ................. A61K 7/06; A61K 7/00
[52] U.S. Cl. ................. 424/70.7; 424/70.1; 424/70.19; 424/401; 514/844; 514/937
[58] Field of Search ................. 424/401, 70.1, 424/70.7, 70.19; 514/844, 937

[56] References Cited

U.S. PATENT DOCUMENTS

| | | | |
|---|---|---|---|
| 3,639,572 | 2/1972 | Heinrich et al. | 424/63 |
| 5,378,484 | 1/1995 | Suwa et al. | 426/329 |
| 5,453,498 | 9/1995 | Nakamura et al. | 536/119 |
| 5,534,247 | 7/1996 | Franjac et al. | 424/70.7 |
| 5,612,021 | 3/1997 | Mellul | 424/61 |
| 5,620,693 | 4/1997 | Piot et al. | 424/401 |
| 5,858,339 | 1/1999 | Piot et al. | 424/70.7 |
| 5,866,111 | 2/1999 | Felardos et al. | 424/70.22 |

FOREIGN PATENT DOCUMENTS

| | | |
|---|---|---|
| 57-21310 | 2/1982 | Japan . |
| 80/00452 | 3/1980 | WIPO . |

*Primary Examiner*—Shelley A. Dodson
*Assistant Examiner*—Marina Lamm
*Attorney, Agent, or Firm*—Foley & Lardner

[57] ABSTRACT

An eyelash cosmetic composition containing 0.5 to 10% by weight of a water-dispersible or water-soluble sucrose fatty acid ester and 0.5 to 10% by weight of a fatty acid soap and, optionally containing a water-dispersible clay mineral and/or a synthetic resin emulsion.

4 Claims, No Drawings

EYELASH COSMETIC COMPOSITION

BACKGROUND OF THE INVENTION

1. Field of the Invention

The present invention relates to an eyelash cosmetic composition. More specifically, it relates to an eyelash cosmetic composition superior in the easy application, the easy brushing of eyelashes, and the easy overlap application at the time of the application to eyelashes, and uniformity of finish and voluminous feelings after application.

2. Description of the Related Art

Eyelash cosmetics, typically represented by mascara, are required provide effects, i.e., to make the eyelashes appear thicker and longer, to give a voluminous feeling to the eyelashes, and further to provide functional effects such as a cosmetic durability effect (e.g., water resistance and skin oil resistance), curling effect (i.e., quick dryability and effect of making eyelashes curl and be held turned upward). Recently, especially the improvement in the provision of the voluminous feeling of the eyelashes is strongly demanded.

In the general water-based mascaras, one of the methods for improving the voluminous feeling is to increase the viscosity of the composition of formulating thereinto a larger amount of, for example, water dispersible clay minerals. However, according to this method, great improvement can not be expected in the voluminous feelings. When the viscosity is too high, there is sometimes a lack of smoothness at the time of application and a poor finish, and conversely a loss of sense of volume.

Further, there is a method for increasing the stickiness and improving the voluminous feelings by formulating thereinto a larger amount of a water-soluble polymer, synthetic resin polymer emulsion, etc. However, according to this method, a great improvement in voluminous feelings cannot be expected, the overlapping application becomes difficult, and the finish becomes poor.

Further, there is a method for increasing the viscosity of the composition by increasing the addition amount of wax, oil, etc. However, according to this method, a large voluminous feeling cannot be expected and conversely the decrease in the oil resistance and sebam oil resistance is unfortunately resulted.

SUMMARY OF THE INVENTION

Accordingly, the objects of the present invention are to obviate the above-mentioned problems in the prior and to provide an eyelash cosmetic composition superior in the easy application, the easy brushing of eyelashes and the easy overlap application at the time of the application to eyelashes and superior in the uniformity of finish and voluminous feelings after application.

In accordance with the present invention, there is provided an eyelash cosmetic composition comprising 0.5 to 10% by weight of a water-dispersible or water-soluble sucrose fatty acid ester, and 0.5 to 10% by weight of a fatty acid soap.

DESCRIPTION OF THE PREFERRED EMBODIMENTS

The present inventors engaged in intensive research to solve the above problems and, as a result, found that by formulating predetermined amounts of a water-dispersible or water-soluble sucrose fatty acid ester having a low degree of substitution and a fatty acid soap, the above problems were able to be solved and thus the present invention has been completed.

That is, the present invention relates to an eyelash cosmetic composition containing 0.5 to 10% by weight of a water-dispersible or water-soluble sucrose fatty acid ester and 0.5 to 10% by weight of a fatty acid soap.

The water-dispersible or water-soluble sucrose fatty acid ester usable in the present invention is preferably include a sucrose fatty acid ester having an average degree of substitution of 1 to 1.8 and a monoester content of not less than 40% by weight.

The present invention will be explained in detail below.

The sucrose fatty acid ester used in the present invention should be water-dispersible or water-soluble. The sucrose fatty acid esters are preferably those having an average degree of substitution of 1 to 1.8, and a monoester content of 40% to 100% by weight, in view of the further improvements in the water-dispersibility or water-solubility. The "degree of substitution" of the ester referred to here means the average value of the number of bonds of the ester-bonded fatty acid per molecule of sucrose constituting the sucrose fatty acid ester.

The fatty acids constituting the water-dispersible or water-soluble sucrose fatty acid esters include, $C_8$ to $C_{22}$ saturated or unsaturated fatty acids. Examples of such fatty acids are caprylic acid, capric acid, lauric acid, myristic acid, palmitic acid, stearic acid, behenic acid, 2-ethyl hexanoic acid, isostearic acid, oleic acid, etc. Among these, stearic acid, palmitic acid, etc. are preferable from the viewpoint of the solubility, stability, etc. These fatty acids may be used alone or in any mixture thereof.

The content of the water-dispersible or water-soluble sucrose fatty acid ester is 0.5 to 10% by weight, preferably 1 to 7% by weight from the viewpoint of the applicability, based upon the total weight of the eyelash cosmetic composition of the present invention. If the amount is less than 0.5% by weight, the voluminous feeling after finish is inferior. On the other hand, if the amount is more than 10% by weight, the viscosity of the composition becomes too high and the production thereof becomes difficult.

The fatty acids which may be used in the fatty acid soaps of the present invention include preferably those having an alkyl or alkenyl group having 12 or more carbon atoms, preferably 14 to 22 carbon atoms. Examples of such fatty acid soaps are monofatty acids such as lauric acid, myristic acid, palmitic acid, stearic acid, behenic acid, oleic acid, 12-hydroxystearic acid, undecylenic acid, tall acid, isostearic acid, linoleic acid, linolenic acid, eicosapentaenoic acid (EPA), docosahexaenoic acid (DHA), or composite fatty acids such as coconut oil fatty acid, palm oil fatty acid, tallow fatty acid, etc. Especially, the use of stearic acid, isostearic acid is preferable due to the stability and the easy overlapping application. These fatty acids may be used alone or in any mixture thereof. For example, when two or more fatty acids such as stearic acid and isostearic acid are used in combination, the voluminous feeling after finish can be further improved.

Examples of the counter ions of the fatty acid soap are sodium, potassium, triethanolamine, etc.

The "fatty acid soap" used in the present invention means a fatty acid which is neutralized in part or whole with a base. In the present invention, those having a fatty acid, which remains unreacted without being neutralized, are also used. Especially, those having a neutralization rate of 30% to 100% are preferred from the viewpoint of the pH stability. The content of the fatty acid soap in the cosmetic composition of the present invention means the total amount of the fatty acids and the bases, which neutralize all or part of the acidic fatty acids.

The fatty acid soaps usable in the present invention can be obtained by mixing, for example, a fatty acid and an aqueous alkaline solution containing the above-mentioned counter ions with other ingredients to produce the fatty acid soap in the system, but, of course, is not limited to this method.

The content of the fatty acid soap is 0.5 to 10% by weight, preferably 1 to 8% by weight from the viewpoint of applicability, based upon the weight of the eyelash cosmetic composition of the present invention. If the content is less than 0.5% by weight, the smoothness at the time of application becomes insufficient and the easy overlap application property becomes insufficient. On the other hand, if the content is more than 10% by weight, the dryability becomes poor and the voluminous feelings are sometimes impaired.

The eyelash cosmetic composition of the present invention may further preferably contain a water dispersible clay mineral from the viewpoint of increasing the voluminous feelings. Examples of the water dispersible clay mineral are bentonite, hectorite, montmorillonite. By the formulation of these water dispersible clay minerals, the system can be stabilized as a result. These water dispersible clay minerals may be used alone or in any mixture thereof.

The content of the water dispersible clay mineral is preferably 0.1 to 1.5% by weight, more preferably 0.2 to 1% by weight, from the viewpoints of the provision of the voluminous feelings and the applicability based upon the total weight of the eyelash cosmetic composition of the present invention. If the content is less than 0.1% by weight, the effect by the addition of the water dispersible clay mineral cannot be sufficiently obtained. On the other hand, when the content is more than 1.5% by weight, it is not expected to further improve the voluminous feelings and the applicability may be decreased.

The eyelash cosmetic composition of the present invention further preferably contains a synthetic resin emulsion having a film-forming capability from the viewpoint of further improving the applicability (i.e., elasticity of film and curling effect) and durability of cosmetic composition. The synthetic resin emulsions, useable in the present invention include, for example, those listed in British Patent No. 1110240, U.S. Pat. No. 3,639,572, Japanese Unexamined Patent Publication (Kokai) No. 48-36347, Japanese Unexamined Patent Publication (Kokai) No. 1-203313, etc. Examples thereof are, for example, ethyl acrylate, methyl methacrylate, butyl methacrylate, methacrylic acid, a copolymer emulsion of a vinylidene chloride and vinyl chloride. As the other synthetic resin emulsion, for example, an alkyl acrylate copolymer emulsion, an alkylacrylate-styrene copolymer emulsion, an ethylpolyacrylate emulsion, an alkyl polyacrylate emulsion, a polyvinyl acetate resin emulsion, etc. These synthetic resin emulsions may be used alone or in any mixture thereof.

The content of the synthetic resin emulsion is preferably 1 to 30% by weight, more preferably 2.5 to 15% by weight, in terms of a solid content, based upon the total amount of the eyelash cosmetic composition of the present invention, from the viewpoint of the further improvement of the applicability and durability of the cosmetic composition.

The eyelash cosmetic composition of the present invention may optionally contain any ingredients which may be usually formulated into conventional makeup cosmetic compositions in the range of quantity and quality, not impairing the effect of the present invention. Examples of such ingredients are a preservative, coloring agent, alcohol, polyhydric alcohol, medicine, surfactant, water-soluble polymer, thickener, clay mineral, perfume, antioxidant, UV absorbent, humectant, wax, oils and fats, hydrocarbon oils, and other oil ingredients.

The coloring agent is not particularly limited so long as it is a coloring agent generally used for a makeup cosmetic composition. Examples of the coloring agents are inorganic pigments such as talc, mica, kaolin, calcium carbonate, zinc white, titanium dioxide, red iron oxide, yellow iron oxide, black iron oxide, ultramarine blue, Prussian blue, carbon black, lower titanium oxide, Cobalt Violet, chromium oxide, chromium hydroxide, cobalt titanium oxide, bismuth oxychloride, titanium-mica based pearl pigment; organic pigments such as Lithol rubine B (Red No. 201), Lithol rubine BCA (Red No. 202), Lake red CBA (Red No. 204), Lithol red (Red No. 205), Deep maroon (Red No. 220), Helidone pink CN (Red No. 226), Permatone Red (Red No. 228), Permanent red F5R (Red No. 405), Permanent orange (Orange No. 203), Benzidine yellow G (Yellow No. 205), Tartrazine (Yellow No. 4), Sunset yellow FCF (Yellow No. 5), Brilliant blue FCF (Blue No. 1), Phthalocyanine blue (Blue No. 404), Fast green FCF (Green No. 3), or other zirconium, barium or aluminum lakes; natural dyes such as chlorophyl, $\beta$-carotin; resin powders such as nylon, cellulose, polyethylene; dyestuffs, etc. These coloring agents may be used alone or in any mixture thereof.

The coloring agent may be preferably contained in an amount of 0.001 to 50% by weight, based upon the total weight of the eyelash cosmetic of the present invention.

EXAMPLES

The present invention will now be further explained in detail, but is by no means limited to, the following Examples. The content and the amount are in % by weight.

The methods of testing and methods of evaluation of the present invention will be first explained below.

Voluminous feeling

The samples (i.e., mascara) were applied 10 times using a panel of 20 woman's experts and the state was visually evaluated according to the following criteria:

Evaluation

Rank Number of Positive Response (Total 20)

Excellent (⊚): 16 or more

Good (○): 9 to 15

Fair (Δ): 5 to 8

Poor (x): Not more than 4

Easy Overlap Application

The samples (i.e., mascara) were applied 10 times in a panel of 20 woman's experts and the easy overlap application at the time of application was evaluated functionally according to the following criteria:

Evaluation

Rank Number of Positive Response (Total 20)

Excellent (⊚): 16 or more

Good (○): 9 to 15

Fair (Δ): 5 to 8

Poor (x): Not more than 4

Finish

The samples (i.e., mascara) were applied 10 times by a panel of 20 woman's experts and the state was visually evaluated according to the following criteria:

Evaluation

Rank Number Positive Response (Total 20)

Excellent (◎): 16 or more
Good (○): 9 to 15
Fair (Δ): 5 to 8
Poor (x): Not more than 4

Applicability

The easy applicability, easy drying, etc. when applying the samples (i.e., mascara) to the eyelashes by a panel of 20 woman's experts were evaluated according to the following criteria:

Evaluation

Rank Number of Positive Response

Good (○): 12 or more
Fair (Δ): 6 to 11
Poor (x): Not more than 5

Examples 1 to 6 and Comparative Examples 1 to 4

The eyelash cosmetic compositions (i.e., mascara) having the compositions shown in Tables 1 and 2 were prepared and the following criteria used for evaluation of the voluminous feeling, easy overlap application, finish, and applicability. The results are shown in Tables 1 and 2.

Note that in Tables 1 and 2, (*) "Sucrose hydrogenated tallow fatty acid ester" had a degree of substitution of 1.3 and a monoester content of 70% by weight.

TABLE 1

|  | Examples | | | | | |
| --- | --- | --- | --- | --- | --- | --- |
|  | 1 | 2 | 3 | 4 | 5 | 6 |
|  | (wt. %) | | | | | |
| (1) Palmitic acid | 2 | 3 | 4 | 3 | 3 | 4 |
| (2) Sucrose hydrogenated tallow fatty acid ester (*) | 0.5 | 5 | 7 | 3 | 3 | 7 |
| (3) Ceresin wax | 15 | 12 | 12 | 20 | 20 | 12 |
| (4) Polyvinyl acrylate emulsion (in terms of a solid) | 4 | 8 | 4.8 | 3.2 | — | 4.8 |
| (5) Sorbitan monostearate | 1 | 1 | 1 | 1 | 1 | 1 |
| (6) POE (20) sorbitan monostearate | 0 | 1 | 1 | 1 | 1 | 1 |
| (7) Bentonite | 0.8 | 0.5 | 0.5 | 0.3 | 0.5 | — |
| (8) Ethanol | 2 | 2 | 2 | 2 | 2 | 2 |
| (9) Black iron oxide | 10 | 10 | 10 | 10 | 10 | — |
| (10) Sodium hydroxide | 0.2 | 0.3 | 0.4 | 0.3 | 0.3 | 0.4 |
| (11) Methyl paraben | q.s. | q.s. | q.s. | q.s. | q.s. | q.s. |
| (12) Ion exchanged water | balance | balance | balance | balance | balance | balance |
| Voluminous feeling | ◎ | ◎ | ◎ | ◎ | ◎ | ◎ |
| Easy overlap application | ◎ | ◎ | ◎ | ◎ | ◎ | ◎ |
| Finish | ◎ | ○ | ◎ | ◎ | ◎ | ◎ |
| Applicability | ○ | ○ | ○ | ○ | ○ | ○ |

TABLE 2

|  | Comparative Examples | | | |
| --- | --- | --- | --- | --- |
|  | 1 | 2 | 3 | 4 |
|  | (wt. %) | | | |
| (1) Palmitic acid | — | 2 | — | — |
| (2) Sucrose hydrogenated tallow fatty acid ester (*) | — | — | 3 | 3 |
| (3) Ceresin wax | 25 | 20 | 15 | 15 |
| (4) Polyvinyl acrylate emulsion (in terms of a solid) | 4 | 8 | 6 | 12 |
| (5) Sorbitan monostearate | 1 | 1 | 1 | 1 |
| (6) POE (20) sorbitan monostearate | 1 | 0 | 1 | 1 |
| (7) Bentonite | 0.4 | 0.4 | 0.5 | 0.3 |
| (8) Ethanol | 2 | 2 | 2 | 2 |
| (9) Black iron oxide | 10 | 10 | 10 | 10 |
| (10) Sodium hydroxide | — | 0.2 | — | — |
| (11) Methyl paraben | q.s. | q.s. | q.s. | q.s. |
| (12) Ion exchanged water | balance | balance | balance | balance |

TABLE 2-continued

|  | Comparative Examples | | | |
|---|---|---|---|---|
|  | 1 | 2 | 3 | 4 |
| Voluminous feeling | Δ | x | x | ○ |
| Easy overlap application | Δ | Δ | ○ | x |
| Finish | x | Δ | Δ | x |
| Applicability | Δ | Δ | ○ | x |

Process of Production

Components (1), (3), and (5) were heated at 90° C. to melt, then this was added to a dispersion of (2), (6), (7), (9), and (10) to (12) heated to 85° C. This was then dispersed by a homomixer, then (4) and (8) added, then the result was stirred and cooled to 40° C. to obtain the eyelash cosmetic composition (i.e., mascara).

Evaluation

As clear from the results shown in Tables 1 and 2, Comparative Example 1 was a formulation containing neither the sucrose fatty acid ester nor the fatty acid soap and containing a large amount of wax, but this was inferior in the voluminous feeling and finish and not satisfactory in easy overlap application. Comparative Example 2 was a formulation not containing a low degree of substitution of sucrose fatty acid ester and containing a fatty acid soap. While the easy overlap application was somewhat improved, the voluminous feeling conversely fell. Comparative Example 3 was a formulation not containing a fatty acid soap, but containing sucrose fatty acid ester having a low degree of substitution, the finish was improved, but the voluminous feeling and the easy overlap application were not satisfactory. Comparative Example 4 was a formulation not containing a fatty acid soap, but containing sucrose fatty acid ester having a low degree of substitution and containing a large amount of a synthetic resin emulsion. The voluminous feeling was improved, but there was no great improvement. Conversely, a decrease in the easy overlap application, finish, and applicability were resulted.

On the other hand, Examples 1 to 6 were satisfactory in all of the voluminous feeling, easy overlap application, finish, and applicability. It was learned that the combination of predetermined amounts of the fatty acid soap and the sucrose fatty acid ester having a low degree of substitution was extremely effective in improving these characteristics.

| Example 7: Water Based Mascara | | wt. % |
|---|---|---|
| (1) | Stearic acid | 3 |
| (2) | Cetyl-α-monoglycerine ether | 1 |
| (3) | Sucrose oleic acid ester (degree of substitution 1.2, monoester content 40% by weight) | 3 |
| (4) | Beeswax | 15 |
| (5) | Polyacrylic acid ester emulsion (in terms of a solid) | 8 |
| (6) | POE (20) sorbitan monostearate | 1 |
| (7) | Isopropanol | 2 |
| (8) | Bentonite | 0.5 |
| (9) | Black iron oxide | 8 |
| (10) | Ethyl paraben | q.s. |
| (11) | Ion exchanged water | balance |
| (12) | Sodium hydroxide | 0.3 |
| (13) | Perfume | q.s. |

Process of Production (1), (2), and (4) were heated at 90° C. to melt, then this was added to a dispersion of (3), (6), and (8) to (12) heated to 85° C. This was then dispersed by a homomixer, then (5), (7), and (13) added, then the mixture was stirred and cooled to 40° C. to obtain the eyelash cosmetic composition (i.e., mascara).

This was evaluated by the above criteria for the voluminous feeling, easy overlap application, finish, and applicability, whereupon the voluminous feeling was excellent, the easy overlap application was excellent, the finish was excellent, and the applicability was excellent.

| Example 8: Water Based Mascara | | wt. % |
|---|---|---|
| (1) | Palmitic acid | 2 |
| (2) | Isostearic acid | 2 |
| (3) | Sucrose stearic acid ester (degree of substitution 1.2, monoester content 60% by weight) | 4 |
| (4) | Carnuaba wax | 4 |
| (5) | Polyacrylic acid ester emulsion (in terms of a solid) | 8 |
| (6) | POE (20) sorbitan monostearate | 1 |
| (7) | Phenoxy ethanol | 1 |
| (8) | Hectorite | 0.2 |
| (9) | Black iron oxide | 8 |
| (10) | Ethyl paraben | 0.3 |
| (11) | Ion exchanged water | balance |
| (12) | Triethanol amine | 0.4 |

Process of Production (1), (2), and (4) were heated at 90° C. to melt, then this was added to a dispersion of (3), (6), and (8) to (12) heated to 85° C. This was then dispersed by a homomixer, then (5) and (7) added, then the resultant mixture was stirred and cooled to 40° C. to obtain the eyelash cosmetic composition (mascara).

This was evaluated according to the above criteria for the voluminous feeling, easy overlap application, finish, and applicability, whereupon the voluminous feeling was excellent, the easy overlap application was excellent, the finish was excellent, and the applicability was excellent.

| Example 9: Water Based Mascara | | wt. % |
|---|---|---|
| (1) | Stearic acid | 3 |
| (2) | Cetyl-α-monoglycerine ether | |
| (3) | Sucrose oleic acid ester (degree of substitution 1.2, monoester content 40% by weight) | 3 |
| (4) | Sucrose pentastearate | 10 |
| (5) | Polyacrylic acid ester emulsion (in terms of solid) | 8 |
| (6) | POE (20) sorbitan monostearate | 1 |
| (7) | Isopropanol | 2 |
| (8) | Bentonite | 0.5 |
| (9) | Black iron oxide | 8 |
| (10) | Ethyl paraben | 0.3 |
| (11) | Ion exchanged water | balance |
| (12) | Potassium hydroxide | 0.3 |
| (13) | Perfume | q.s. |

Process of Production (1), (2), and (4) were heated at 90° C. to melt, then this was added to a dispersion of (3), (6), and (8) to (12) heated to 85° C. This was then dispersed by a homomixer, then (5), (7), and (13) added, then the mixture was stirred and cooled to 40° C. to obtain the eyelash cosmetic composition (mascara).

| Example 10: Water Based Mascara | | wt. % |
|---|---|---|
| (1) | Stearic acid | 3 |
| (2) | Cetyl-α-monoglycerine ether | 1 |
| (3) | Sucrose oleic acid ester (degree od substitution 1.2, monoester content 40% by weight) | 3 |
| (4) | Sucrose pentastearate | 10 |
| (5) | Polyacrylic acid ester emulsion (in terms of solid) | 8 |
| (6) | POE (20) sorbitan monostearate | 1 |
| (7) | Isopropanol | 2 |
| (8) | Bentonite | 0.5 |
| (9) | Black iron oxide | 8 |
| (10) | Ethyl paraben | 0.3 |
| (11) | Ion exchanged water | balance |
| (12) | Potassium hydroxide | 0.3 |
| (13) | Xylitol | 1.0 |
| (14) | Perfume | q.s. |

Process of Production (1), (2), and (4) were heated at 90° C. to melt, then this was added to a dispersion of (3), (6), and (8) to (13) heated to 85° C. This was then dispersed by a homomixer, then (5), (7), and (14) added, then the mixture was stirred and cooled to 40° C. to obtain the eyelash cosmetic composition (mascara).

| Example 11: Water Based Emulsion | | wt. % |
|---|---|---|
| (1) | Stearic acid | 3 |
| (2) | Cetyl-α-monoglycerine ether | — |
| (3) | Sucrose oleic acid ester (degree of substitution 1.2, monoester content 40% by weight) | 3 |
| (4) | Candelilla wax | 10 |
| (5) | Acrylic acid alkyl-styrene copolymer emulsion (in terms of solid) | 8 |
| (6) | POE (20) sorbitan monostearate | 1 |
| (7) | Isopropanol | 2 |
| (8) | Bentonite | 0.5 |
| (9) | Black iron oxide | 8 |
| (10) | Ethyl paraben | 0.3 |
| (11) | Ion exchanged water | balance |
| (12) | Potassium hydroxide | 0.3 |
| (13) | Perfume | q.s. |
| (14) | Soybean phospholipid | 1.0 |

Process of Production (1), (2), and (4) were heated at 90° C. to melt, then this was added to a dispersion of (3), (6), (8) to (12), and (14) heated to 85° C. This was then dispersed by a homomixer, then (5), (7), and (13) added, then the mixture was stirred and cooled to 40° C. to obtain the eyelash cosmetic composition (mascara).

| Example 12: Water Based Mascara | | wt. % |
|---|---|---|
| (1) | Stearic acid | 3 |
| (2) | Cetyl-α-monoglycerine ether | 1 |
| (3) | Sucrose oleic acid ester (degree of substitution 1.2, monoester content 40% by weight) | 3 |
| (4) | Candelilla wax | 10 |
| (5) | Acrylic acid alkyl-styrene copolymer emulsion (in terms of solid) | 8 |
| (6) | POE (20) sorbitan monostearate | 1 |
| (7) | Isopropanol | 2 |
| (8) | Bentonite | 0.5 |
| (9) | Black iron oxide | 8 |
| (10) | Ethyl paraben | 0.3 |
| (11) | Ion exchanged water | balance |
| (12) | Potassium hydroxide | 0.3 |
| (13) | Perfume | q.s. |
| (14) | Macadamia nut oil fatty acid cholesteryl | 1.0 |

Process of Production (1), (2), (4) and (14) were heated at 90° C. to melt, then this was added to a dispersion of (3), (6), and (8) to (12) heated to 85° C. This was then dispersed by a homomixer, then (5), (7), and (13) added, then the mixture was stirred and cooled to 40° C. to obtain the eyelash cosmetic composition (mascara).

| Example 13: Water Based Mascara | | wt. % |
|---|---|---|
| (1) | Stearic acid | 3 |
| (2) | Cetyl-α-monoglycerine ether | 1 |
| (3) | Sucrose oleic acid ester (degree of substitution 1.2, monoester content 40% by weight) | 3 |
| (4) | Carnuaba wax | 8 |
| (5) | Acrylic acid alkyl copolymer emulsion (in terms of solid) | 7 |
| (6) | POE (20) sorbitan monostearate | 1 |
| (7) | Isopropanol | 2 |
| (8) | Bentonite | 0.5 |
| (9) | Black iron oxide | 8 |
| (10) | Ethyl paraben | 0.3 |
| (11) | Ion exchanged water | balance |
| (12) | Potassium hydroxide | 0.3 |
| (13) | Perfume | q.s. |
| (14) | Macadamia nut oil fatty acid phytosteryl | 1.0 |

Process of Production (1), (2), (4), and (14) were heated at 90° C. to melt, then this was added to a dispersion of (3), (6), and (8) to (12) heated to 85° C. This was then dispersed by a homomixer, then (5), (7), and (13) added, then the mixture was stirred and cooled to 40° C. to obtain the eyelash cosmetic composition (mascara).

As explained above, according to the present invention, it is possible to provide an eyelash cosmetic composition which is superior in the easy application, the easy overlap application, etc. at the time of application of the eyelash cosmetic composition and the uniformity of the finish and the improvement in the voluminous feeling after application.

We claim:

1. An eyelash cosmetic composition comprising:

0.5 to 10% by weight of a water-dispersible or water-soluble sucrose fatty acid ester having an average degree of substitution of 1 to 1.8 and a monoester content of 40% to 100% by weight, and 0.5 to 10% by weight of a fatty acid soap.

2. An eyelash cosmetic composition as claimed in claim 1, further comprising a water dispersible clay mineral.

3. An eyelash cosmetic composition as claimed in claim 1, further comprising a synthetic resin emulsion.

4. An eyelash cosmetic composition as claimed in claim 2, further comprising a synthetic resin emulsion.

* * * * *